US00PP22976P2

(12) United States Plant Patent
Hendricks

(10) Patent No.: US PP22,976 P2
(45) Date of Patent: Aug. 21, 2012

(54) TUPELO TREE NAMED 'WFH1'

(50) Latin Name: *Nyssa sylvatica*
Varietal Denomination: WFH1

(76) Inventor: William Hendricks, Perry, OH (US)

( * ) Notice: Subject to any disclaimer, the term of this patent is extended or adjusted under 35 U.S.C. 154(b) by 0 days.

(21) Appl. No.: 13/135,762

(22) Filed: Jul. 14, 2011

(51) Int. Cl.
*A01H 5/00* (2006.01)

(52) U.S. Cl. ..... Plt./216

(58) Field of Classification Search ..... Plt./216
See application file for complete search history.

(56) References Cited

U.S. PATENT DOCUMENTS

PP11,391 P * 5/2000 Glenn ..... Plt./216
* cited by examiner

*Primary Examiner* — Howard Locker
(74) *Attorney, Agent, or Firm* — Renner, Otto, Boisselle & Sklar, LLP

(57) ABSTRACT

A tupelo tree named 'WFH1', a tree distinguished by its narrow columnar growth habit.

4 Drawing Sheets

Latin name of the genus and species including the variety denomination of the plant claimed: The tree claimed relates to a new and distinct cultivar of tupelo, botanically known as *Nyssa sylvatica*, and known by the cultivar name 'WFH1'.

This new cultivar was selected as a single, distinctive individual plant out of a nursery row of seven year old seedlings of *Nyssa sylvatica* of local native origin growing at Klyn Nurseries, Inc., in Perry, Ohio. This new cultivar originated as a single plant and was noted as distinctive because of its narrow columnar growth habit.

In contrast to the horizontally-oriented lower branches typical of trees of this species, the branches of this new cultivar emerged from the main stem and immediately turned upward, giving the cultivar a very narrow columnar growth habit, making it uniquely suited for use in landscape situations where space for lateral spread is limited, or where a narrow, vertical tree is desired.

The original 'WFH1' cultivar is approximately thirteen years old and approximately 4.6 meters in height and has a crown that is approximately 2.4 meters in spread at its widest point. The narrow spread of the crown is directly related to the orientation of the secondary branches in relation to the main stem. The secondary branches emerge from the main stem at an angle of approximately 40 to 60 degrees from vertical. The branches that emerge at wider angles after only a few cm deflect back toward the main stem, assuming a more vertical orientation. The 'NXSXF' cultivar of U.S. Plant Pat. No. 11,391 is illustrated and described as having upright secondary branches that emerge at 60 to 80 degrees from the central leader (main stem) at the base of the crown and 20 to 30 degrees at the top, yielding a conical outline. The more vertical orientation of the secondary branches of the 'WFH1' cultivar yields a columnar growth habit that is distinctly more narrow.

The 'WFH1' cultivar has been asexually reproduced at Klyn Nurseries, Inc. in Perry, Ohio, by means of grafting. All plants propagated by this method have displayed the same unique characteristics of the original tree.

Figure 1:
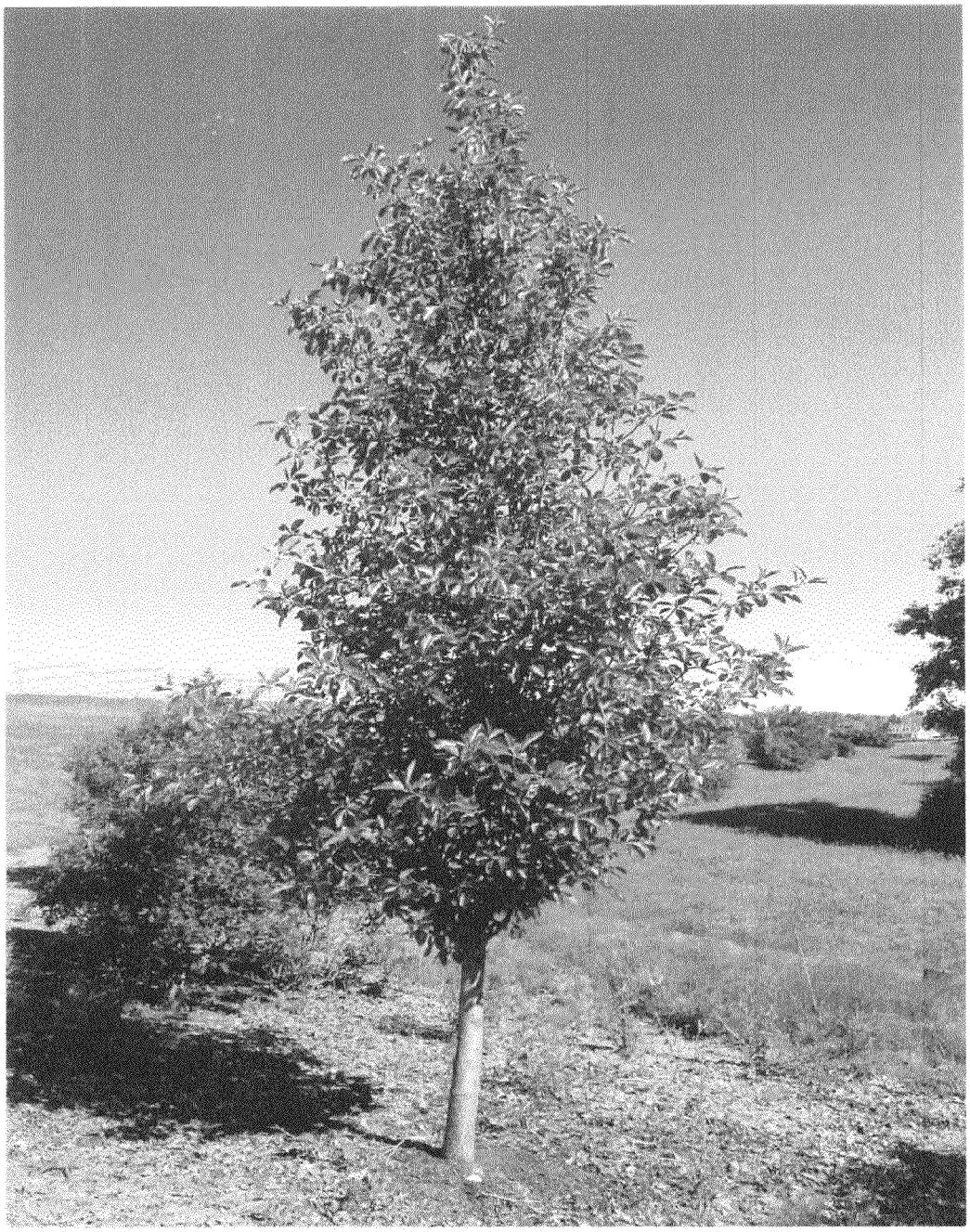
FIG. 1 is a colored photograph illustrating the overall appearance of the 'WFH1' cultivar in the summer.
Figure 2:
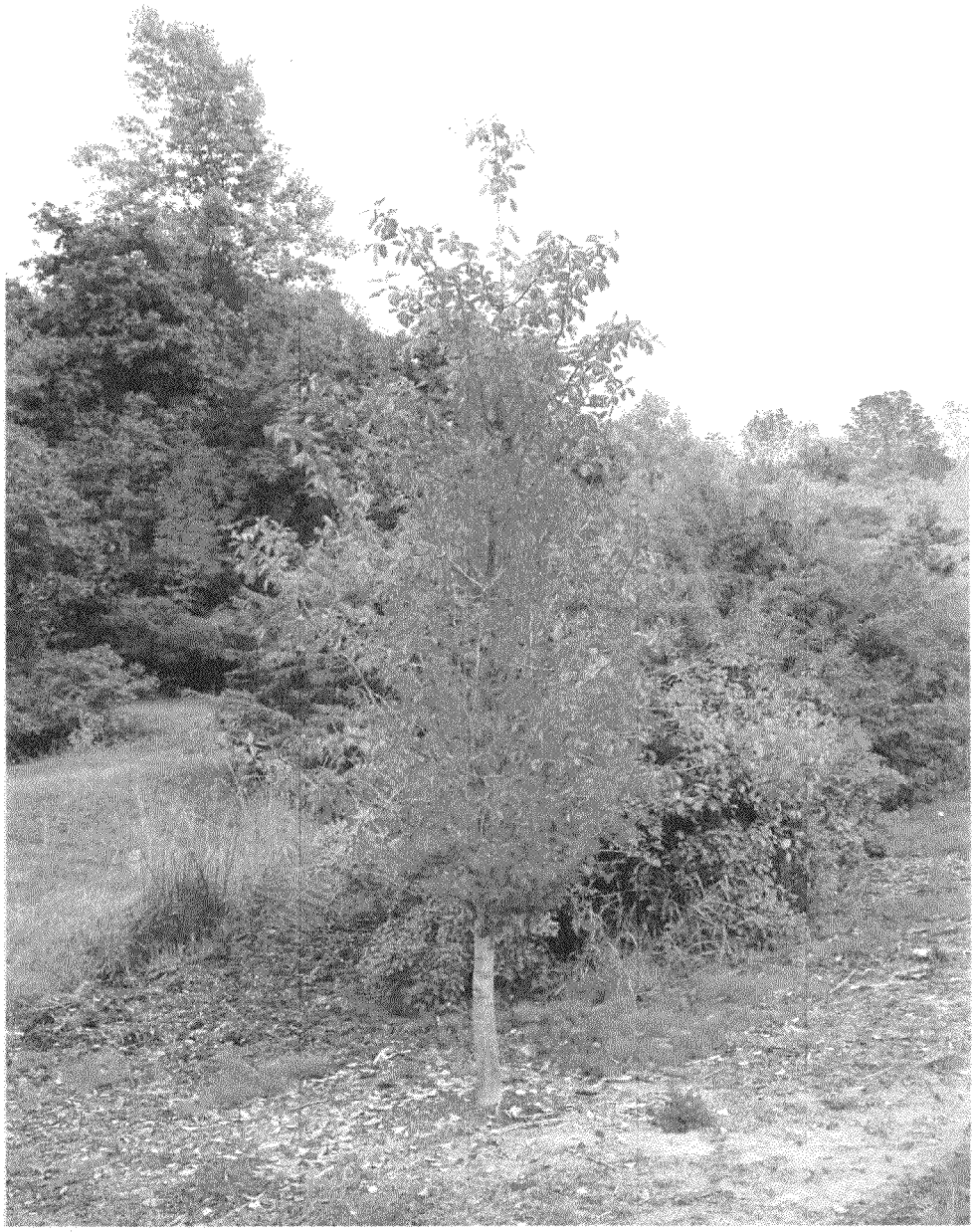
FIG. 2 is a colored photograph illustrating the overall appearance of 'WFH1' in the fall.
Figure 3:
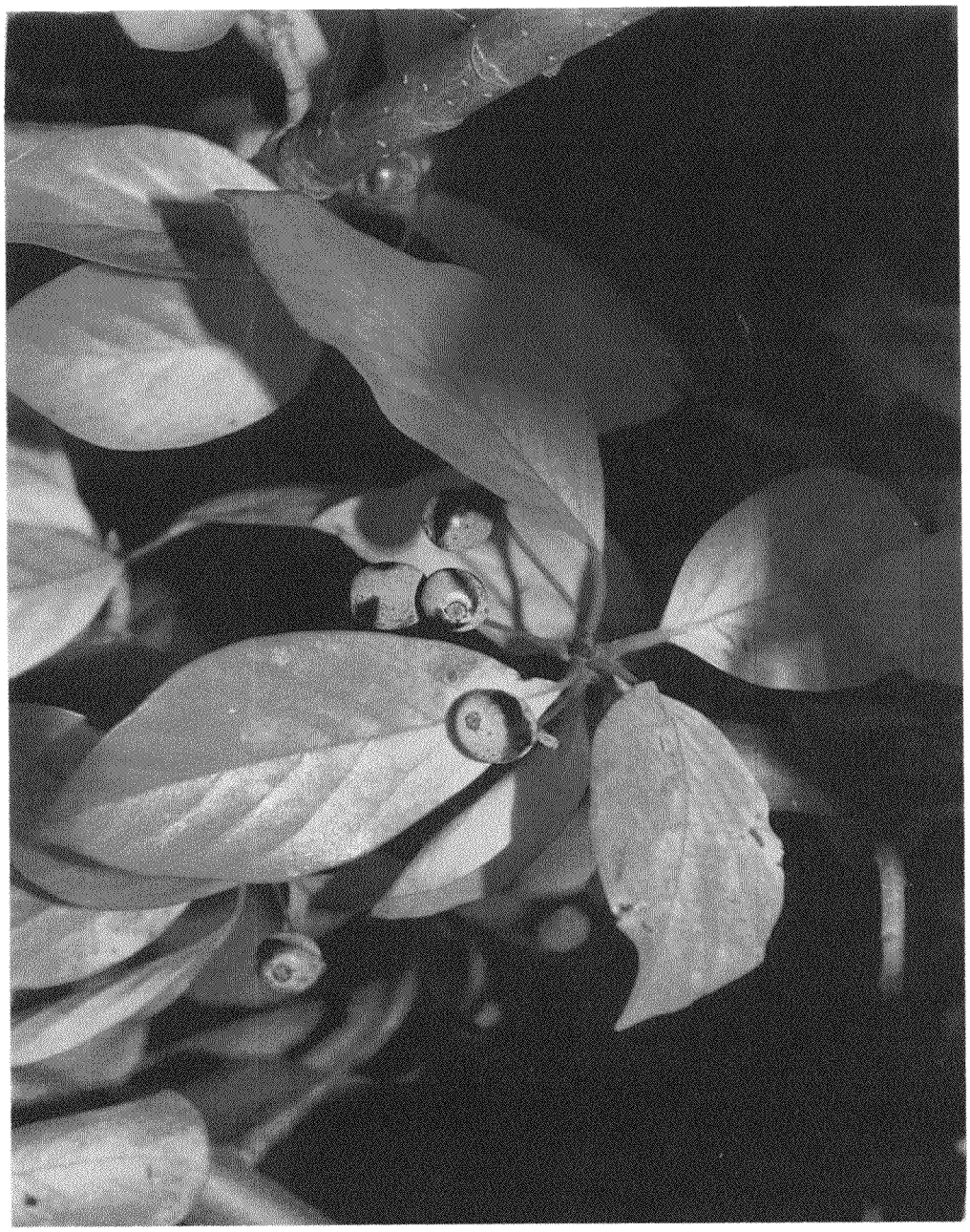
FIG. 3 is a colored photograph illustrating the coloration of the leaves and fruit of 'WFH1' in the fall.
Figure 4:
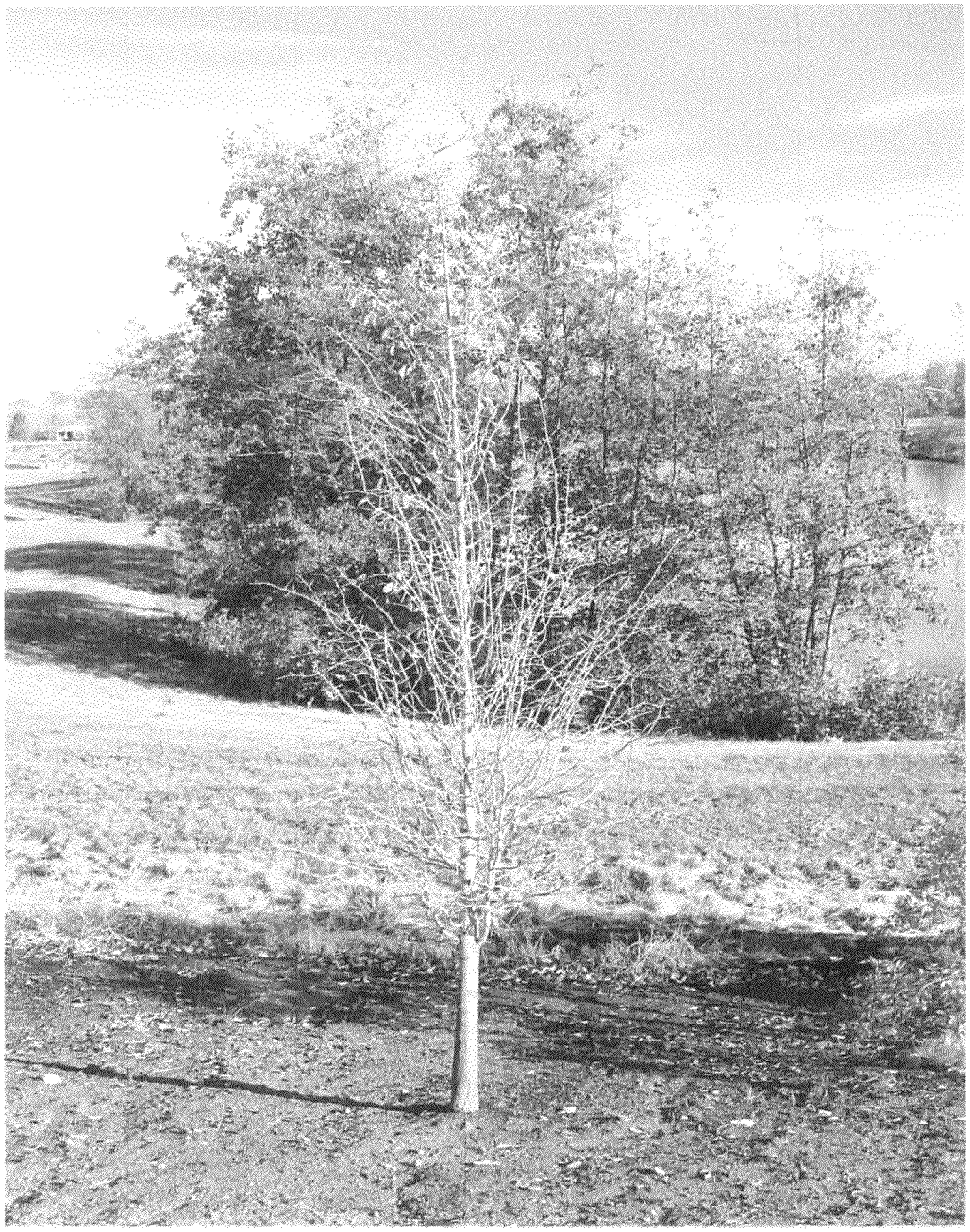
FIG. 4 is a colored photograph illustrating the narrow columnar form of 'WFH1' when dormant.

All of the drawing figures show the colors as truly as is reasonably possible to obtain colored reproductions of this type.

The following is a detailed description of my new 'WFH1' cultivar, with color designations corresponding to the R.H.S. Colour Chart (1986 ed.) published by The Royal Horticultural Society, London, England. Here follows a detailed description of the characteristics of this cultivar, as displayed by the original tree growing at Klyn Nurseries, Inc. in Perry, Ohio. Coloration of leaves and bark may be variable, due to conditions of nutrition, stress, age of plant, location on plant and the presence/absence of sun/shade.

BOTANICAL DESCRIPTION

Parentage: Unknown—originated as a single plant selected out of a nursery row of seven year old seedlings of *Nyssa sylvatica* of local native origin growing at Klyn Nurseries, Inc., in Perry, Ohio.

Hardiness: Hardy in USDA Hardiness Zone 4b (−25 degree F.).

Growth rate: Moderate, more rapid in youth.

Form/size: The original tree is approximately 4.6 meters in height and has a crown that is approximately 2.4 meters in spread at its widest point. The crown spread is directly related to the orientation of the secondary branches in relation to the main stem (central leader). The secondary branches emerge from the main stem at an angle of approximately 40 to 60 degrees from vertical. The branches that emerge at wider angles after only a few cm deflect back toward the main stem, assuming a more vertical orientation.

Bark: The bark of the main stem and secondary branches is smooth and gray in color (between Black Group 202A and 202B).

Leaves: Simple, entire, elliptic to obovate with acute bases and apices, ranging from 5 to 9 cm in length by 2.5 to 5.5 cm in width. Color of leaves in summer is medium-green (Green Group 141B), turning in fall to bright orange red (Red group 44A) with some interior leaves lighter (Yellow Orange Group 17A).

Flowers: This cultivar is a female clone, bearing only female flowers, 2 to 3 flowers per cluster, borne in mid spring. Flowers are tiny, yellow-green (Green Group 143B) and not ornamentally significant.

Fruit: Fertilized flowers give rise to drupes, 10 to 12 mm in length and blue-black (Blue Group 103A) at maturity.

I claim:

1. A tupelo tree named 'WFH1', as shown and described, a tree distinguished by its narrow columnar growth habit.

* * * * *